United States Patent
Yoo et al.

(10) Patent No.: US 12,042,713 B2
(45) Date of Patent: Jul. 23, 2024

(54) METHOD FOR CONTROLLING USER INTERFACE OF EXERCISE DEVICE AND EXERCISE DEVICE PERFORMING SAME

(71) Applicant: DRAX INC., Anyang-si (KR)

(72) Inventors: Seon Kyung Yoo, Seoul (KR); Jae Sang Park, Seongnam-si (KR)

(73) Assignee: DRAX INC., Anyang-si (KR)

( * ) Notice: Subject to any disclaimer, the term of this patent is extended or adjusted under 35 U.S.C. 154(b) by 0 days.

(21) Appl. No.: 18/007,225

(22) PCT Filed: Dec. 2, 2020

(86) PCT No.: PCT/KR2020/017470
§ 371 (c)(1),
(2) Date: Jan. 27, 2023

(87) PCT Pub. No.: WO2022/030695
PCT Pub. Date: Feb. 10, 2022

(65) Prior Publication Data
US 2023/0302343 A1    Sep. 28, 2023

(30) Foreign Application Priority Data

Aug. 5, 2020  (KR) ................... 10-2020-0098134
Nov. 24, 2020 (KR) ................... 10-2020-0159087

(51) Int. Cl.
*A63B 71/06*     (2006.01)
*A63B 24/00*     (2006.01)

(52) U.S. Cl.
CPC ...... *A63B 71/0622* (2013.01); *A63B 24/0087* (2013.01); *A63B 2071/0625* (2013.01);
(Continued)

(58) Field of Classification Search
CPC ............ A63B 71/0622; A63B 24/0087; A63B 2071/0625; A63B 2071/065;
(Continued)

(56) References Cited

U.S. PATENT DOCUMENTS 10,926,128 B2    2/2021 Yoo et al.
2010/0261580 A1* 10/2010 Lannon ............ A63B 21/00076
482/93

(Continued)

FOREIGN PATENT DOCUMENTS

AU    2014280966 A1    5/2016
JP    2004-65382 A     3/2004
(Continued)

OTHER PUBLICATIONS

Office Action dated Jan. 2, 2023 issued by the Korean Patent Office in Korean Application No. 10-2020-0159094.
(Continued)

*Primary Examiner* — Loan B Jimenez
*Assistant Examiner* — Andrew M Kobylarz
(74) *Attorney, Agent, or Firm* — Sughrue Mion, PLLC

(57) ABSTRACT

An exercise machine includes a sensor configured to detect a movement of the exercise machine, a user interface (UI) unit configured to output a UI screen, a memory, and a processor. The processor executes one or more instructions stored in the memory to control the UI unit to display, on the UI screen, a first UI element indicating a user's exercise state corresponding to the detected movement and a second UI element indicating an exercise guide recommended during an exercise using the exercise machine, and change and display a color or shape of at least one of the first UI element and the second UI element, based on a distance between the first UI element and the second UI element on the UI screen.

18 Claims, 16 Drawing Sheets

(52) U.S. Cl.
CPC . *A63B 2071/065* (2013.01); *A63B 2071/0675* (2013.01); *A63B 2220/803* (2013.01); *A63B 2220/833* (2013.01)

(58) Field of Classification Search
CPC ...... A63B 2071/0675; A63B 2220/803; A63B 2220/833; A63B 21/0058; A63B 21/0628; A63B 2024/0068; A63B 24/0062; A63B 2071/0627; A63B 2225/20; A63B 2071/0694; A63B 2220/20; A63B 71/0619; A63B 24/0075; A63B 2220/30
See application file for complete search history.

(56) References Cited

U.S. PATENT DOCUMENTS

| | | | |
|---|---|---|---|
| 2011/0065549 | A1 | 3/2011 | Jung et al. |
| 2012/0220429 | A1 | 8/2012 | Yoshida et al. |
| 2013/0238287 | A1 | 9/2013 | Hoffman et al. |
| 2015/0302331 | A1 | 10/2015 | Randall |
| 2016/0193499 | A1* | 7/2016 | Kim ............... G09B 19/0038 434/247 |
| 2017/0361165 | A1* | 12/2017 | Miller ............. A63B 21/00178 |
| 2018/0126249 | A1* | 5/2018 | Consiglio .......... A63B 22/0023 |
| 2019/0374816 | A1* | 12/2019 | Yun .................... A61B 5/0002 |
| 2021/0016150 | A1 | 1/2021 | Jeong et al. |
| 2023/0201664 | A1* | 6/2023 | Yoo ................... A63B 21/0628 482/8 |
| 2023/0271077 | A1* | 8/2023 | Yoo ................... A63B 24/0062 482/9 |

FOREIGN PATENT DOCUMENTS

| | | | |
|---|---|---|---|
| JP | 2013-103020 | A | 5/2013 |
| JP | 2020-48827 | A | 4/2020 |
| KR | 20-0353290 | Y1 | 6/2004 |
| KR | 10-2011-0029799 | A | 3/2011 |
| KR | 10-2012-0014471 | A | 2/2012 |
| KR | 10-1432129 | B1 | 8/2014 |
| KR | 10-1571362 | B1 | 11/2015 |
| KR | 10-1616545 | B1 | 4/2016 |
| KR | 10-2016-0084703 | A | 7/2016 |
| KR | 10-2017-0135591 | A | 12/2017 |
| KR | 10-1871388 | B1 | 6/2018 |
| KR | 10-2018-0100753 | A | 9/2018 |
| KR | 10-1982168 | B1 | 5/2019 |
| KR | 10-2019-0099555 | A | 8/2019 |
| KR | 10-2019724 | B1 | 9/2019 |
| KR | 10-2031243 | B1 | 10/2019 |
| KR | 10-2020-0022776 | A | 3/2020 |
| KR | 10-2088673 | B1 | 3/2020 |
| KR | 10-2020-0064558 | A | 6/2020 |
| WO | 2009/034309 | A1 | 3/2009 |

OTHER PUBLICATIONS

Office Action dated Sep. 29, 2022 issued by the Korean Patent Office in Korean Application No. 10-2020-0159084.
Office Action dated Sep. 29, 2022 issued by the Korean Patent Office in Korean Application No. 10-2020-0159086.
Office Action dated Sep. 29, 2022 issued by the Korean Patent Office in Korean Application No. 10-2020-0159087.
Office Action dated Sep. 8, 2022 issued by the Korean Patent Office in Korean Application No. 10-2020-0159094.
"Frequently Asked Questions for Social Distancing Configuration", Bitla Solutions Simplified, Jun. 24, 2022, Bitla Software Pvt. Ltd., Retrieved from: https:www.bitlasoft.com/blog/frequently-asked-questions-for-social-distancing-configuration/ , pp. 1-8 (8 pages total).
International Search Report dated Apr. 29, 2021 in International Application No. PCT/KR2020/017470.
Written Opinion of the International Searching Authority dated Apr. 29, 2021 in International Application No. PCT/KR2020/017470.
Office Action issued Jul. 27, 2023 in Korean Application No. 10-2023-0082133.
Extended European Search Report issued Apr. 30, 2024 in European Application No. 20948882.4.

* cited by examiner

METHOD FOR CONTROLLING USER INTERFACE OF EXERCISE DEVICE AND EXERCISE DEVICE PERFORMING SAME

TECHNICAL FIELD

One or more embodiments relate to a method for controlling a user interface of an exercise machine, and an exercise machine performing the method.

BACKGROUND ART

In accordance with the increased quality of life, the interest of people in health is increasing, and numerous people are using various forms of exercise machines to improve their physical strength.

Weight exercise machines are provided in various forms according to the body part or purpose of use to increase the muscle strength, and are configured to strengthen the upper body or the lower body by using the hands or feet. Various types of weight exercise machines are used according to body parts for increasing muscle strength, such as shoulder presses, bench presses, abdominal machines, butterfly machines, arm curl machines, etc.

The weight exercise machines are installed such that a plurality of block-shaped weight plates overlap, and may include a pin structure for selecting some of the plurality of weight plates. A user may select the number or weight of weight members he or she wants to lift by using the pin structure. The user may exercise by moving a selected weight through the exercise structure of the exercise machine.

However, when exercising using such a weight exercise machine, it is difficult for the user to accurately check his/her own exercise state. Also, it is difficult to provide an accurate motivation to the user, for example, to set an exercise goal, and thus, an improvement in an exercise effect is hardly expected.

DISCLOSURE

Technical Problem

Provided are a method of controlling a user interface (UI) of an exercise machine that changes and displays UI elements in the UI of the exercise machine, so that a user using the exercise machine is provided with an exercise guide and is thus able to intuitively know his/her exercise state, and an exercise machine that performs the method.

Technical Solution

According to an aspect of the present disclosure, an exercise machine includes a sensor configured to detect a movement of the exercise machine, a user interface (UI) unit configured to output a UI screen, a memory storing one or more instructions, and a processor configured to execute the one or more instructions to control the UI unit to display, on the UI screen, a first UI element indicating a user's exercise state corresponding to the detected movement and a second UI element indicating an exercise guide recommended during an exercise using the exercise machine. The processor is further configured to change and display a color or shape of at least one of the first UI element and the second UI element, based on a distance between the first UI element and the second UI element on the UI screen.

According to another aspect of the present disclosure, a method of controlling an exercise machine includes outputting a UI screen to a UI unit, detecting a movement of the exercise machine, and displaying, on the UI screen, a first UI element indicating a user's exercise state corresponding to the detected movement and a second UI element indicating an exercise guide recommended during an exercise using the exercise machine. The displaying includes changing and displaying a color or shape of at least one of the first UI element and the second UI element, based on a distance between the first UI element and the second UI element on the UI screen.

According to another aspect of the present disclosure, a computer-readable storage medium storing instructions executable by a processor includes instructions to output a UI screen to a UI unit, instructions to detect a movement of an exercise machine, and instructions to display, on the UI screen, a first UI element indicating a user's exercise state corresponding to the detected movement and a second UI element indicating an exercise guide recommended during an exercise using the exercise machine. The instructions to display, on the UI screen, include changing and displaying a color or shape of at least one of the first UI element and the second UI element, based on a distance between the first UI element and the second UI element on the UI screen.

Advantageous Effects

In a method for controlling a user interface of an exercise machine, and an exercise machine performing the method, according to an embodiment of the present disclosure, an exercise guide and an exercise state are provided through an intuitive user interface (UI), so that a user may perform an effective exercise.

In the method for controlling a user interface of an exercise machine, and the exercise machine performing the method, according to an embodiment of the present disclosure, how much the user adheres to the exercise guide may be effectively informed, and the user may be motivated to exercise according to the exercise guide.

BEST MODE

According to an aspect of the present disclosure, an exercise machine includes a sensor configured to detect a movement of the exercise machine, a user interface (UI) unit configured to output a UI screen, a memory storing one or more instructions, and a processor configured to execute the one or more instructions to control the UI unit to display, on the UI screen, a first UI element indicating a user's exercise state corresponding to the detected movement and a second UI element indicating an exercise guide recommended during an exercise using the exercise machine. The processor is further configured to change and display a color or shape of at least one of the first UI element and the second UI element, based on a distance between the first UI element and the second UI element on the UI screen.

Mode for Invention

Various examples now will be described more fully hereinafter with reference to the accompanying drawings. The examples described hereinafter may be modified in many different forms. To more clearly describe features of examples, matters well known to one of ordinary skill in the art to which the below examples pertain will not be described in detail.

Throughout the specification, when an element is referred to as being "connected" or "coupled" to another element, it can be directly connected or coupled to the other element, or can be connected or coupled to the other element with intervening elements interposed therebetween. In addition, the terms "comprises" and/or "comprising" or "includes" and/or "including" when used in this specification, specify the presence of stated elements, but do not preclude the presence or addition of one or more other elements.

While such terms as "first," "second," etc., may be used to describe various components, such components must not be limited to the above terms. The above terms are used only to distinguish one component from another.

The below embodiments relate to a method of controlling a user interface of an exercise device, and an exercise device performing the method, and a detailed description of matters well known to one of ordinary skill in the art to which the below embodiments pertain will be omitted.

Figure 1:
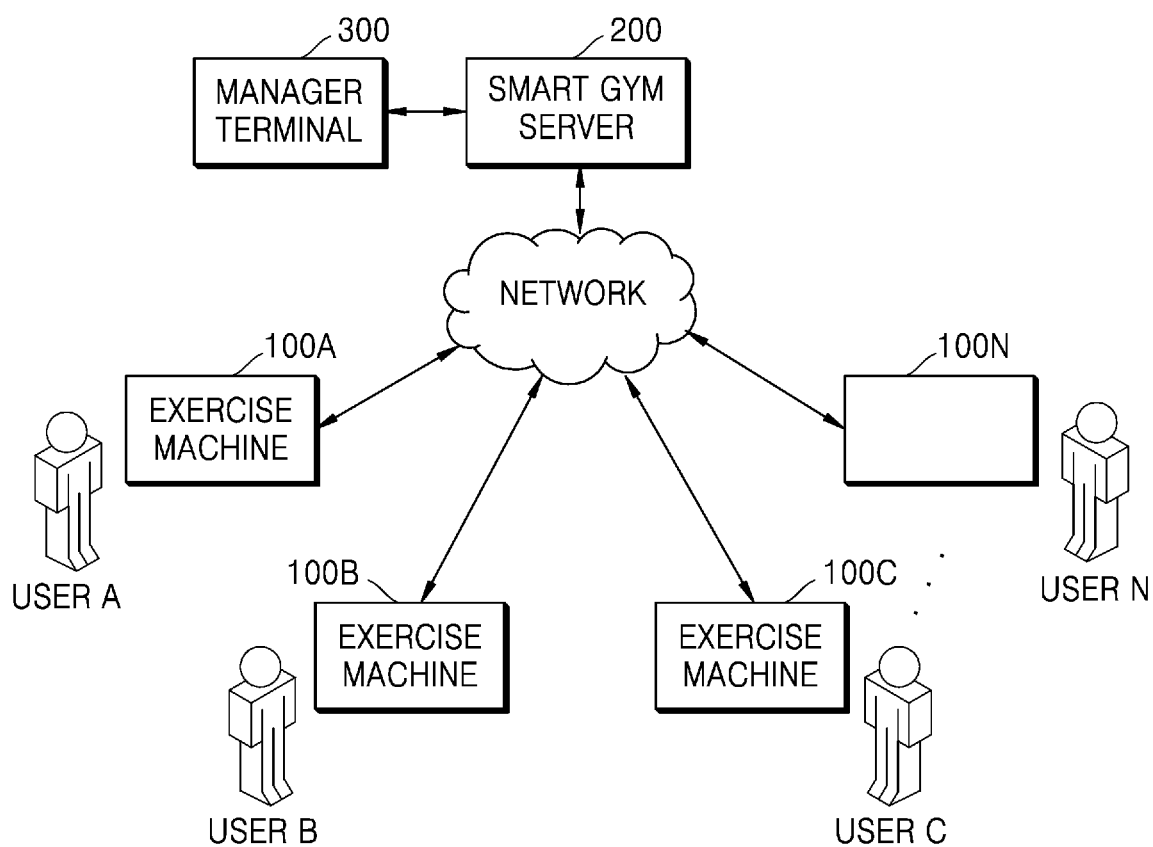
FIG. 1 is a view for explaining a smart gym environment where exercise devices according to an embodiment of the present disclosure are provided.

FIG. 1 is a view for explaining a smart gym environment where exercise devices 100 according to an embodiment of the present disclosure are provided.

Referring to FIG. 1, a plurality of exercise machines 100A, 100B, 100C, . . . , and 100N are connected to a smart gym server 200 through a network. The plurality of exercise machines 100A, 100B, 100C, . . . , and 100N may be weight exercise machines or aerobic exercise machines. A manager such as a health trainer or a smart gym manager may access the smart gym server 200 through a manager terminal 300.

Each of users USER A, USER B, USER C, . . . , and USER N who came to a smart gym to exercise may enter the smart gym after verifying his or her own identity by using a user terminal such as a wearable device or smartphone when entering or exiting the smart gym. For example, by tagging the user terminal to an unmanned terminal such as a kiosk at the entrance of the smart gym by using a near field communication (NFC) or Radio Frequency IDentification (RFID) method, a user may access the smart gym after membership confirmation. Information about the user whose membership has been confirmed may be transmitted from the smart gym server 200 to at least one of the exercise machines 100A, 100B, 100C, . . . , and 100N through a network.

When the user approaches one of the exercise machines 100A, 100B, 100C, . . . , and 100N and tags a wearable device with the exercise machine, the exercise machine may automatically set performs an exercise program customized to a user's ability value and an exercise performance history, based on information received from the smart gym server 200.

The smart gym server 200 may store user information of a plurality of users, device information of the exercise machines 100A, 100B, 100C, . . . , and 100N, and pieces of information used to operate other facilities or the smart gym.

When a manager such as a fitness trainer registers the exercise program customized for the user in the manager terminal 300, exercise process information stored in the smart gym server 200 may be updated. The exercise machines 100A, 100B, 100C, . . . , and 100N may receive exercise process information from the smart gym server 200 connected through a network.

Figure 2:
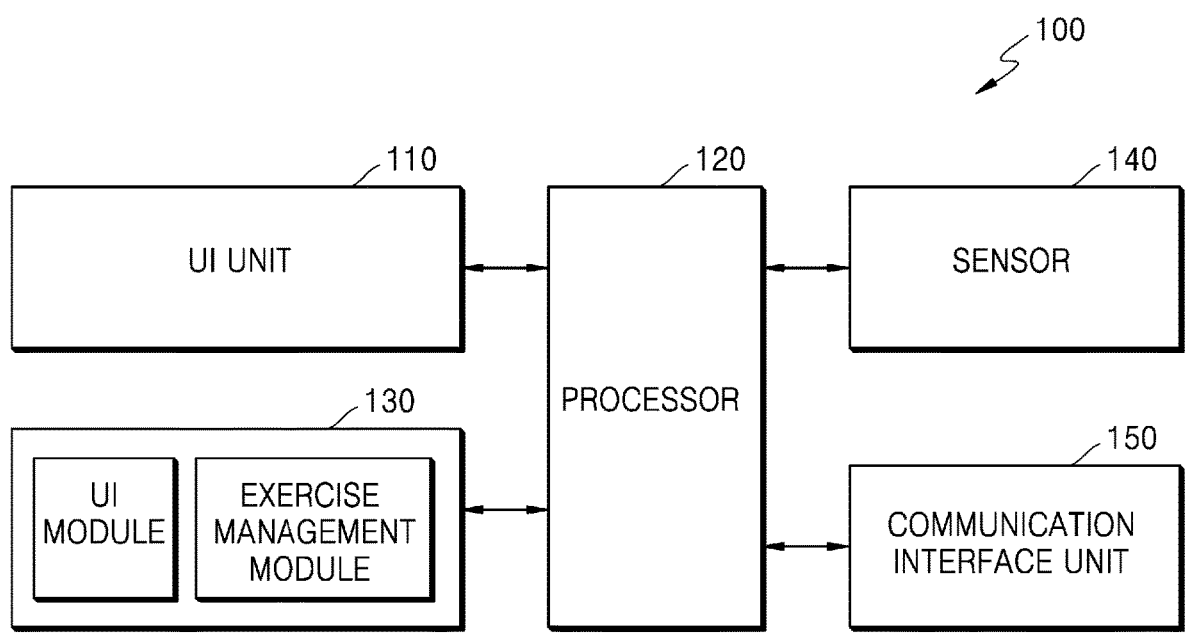
FIG. 2 is a block diagram for explaining a structure and operation of an exercise machine according to an embodiment of the present disclosure.

FIG. 2 is a block diagram for explaining a structure and operation of an exercise machine 100 according to an embodiment of the present disclosure.

Referring to FIG. 2, the exercise machine 100 may include a user interface (UI) unit 110, a processor 120, a memory 130, a sensor 140, and a communication interface unit 150. Although not shown in FIG. 2, the exercise machine 100 may further include a power supply for supplying power to the exercise device 100 or a weight unit for applying a load to a user of the exercise machine 100. The weight unit may be of a mechanical type having a weight plate and a support frame that supports the weight plate or assists a movement of the weight plate and adjusts the weight, but is not limited thereto, and may be of an electronic type including a motor and a member connecting the motor to the exercise machine 100.

The terms "unit", "-er (-or)", and "module" when used in this specification refers to a unit in which at least one function or In operation is performed, and may be implemented as hardware, software, or a combination of hardware and software.

The UI unit 110 may include an input interface for receiving, from a user, an input for an operation of an exercise machine and an input for settings, and an output interface for displaying information, such as an exercise state or an exercise result. For example, the UI unit 110 may be a touch screen, but is not limited thereto.

The processor 120 may manage information for managing various functions provided by the exercise machine 100 or a user's exercise state, by executing one or more instructions stored in the memory 130. Examples of the user's exercise state may include the number of user's exercises or the time of the user's exercise, an exercise level, an exercise speed, and a trajectory of the user's body movement. The processor 120 may include at least one processor. For example, the processor 120 may include at least one of a CPU, a microprocessor, a GPU, application specific integrated circuits (ASICs), a digital signal processor (DSP), and field programmable gate arrays (FPGAs). The processor 120 may control other components included in the exercise machine 100 to perform a function corresponding to a user input received via the UI unit 110. The processor 120 may execute the instructions, a software module, or a program stored in the memory 130, or read data or files from the memory 130, or store a new program or application in the memory 130.

The memory 130 may store one or more instructions. The processor 120 may correspond to an example of a computer capable of executing the instructions stored in the memory 130. The memory 130 may store the instructions, the software module, or the program. The memory 130 may include at least one of random access memory (RAM), static random access memory (SRAM), read-only memory (ROM), flash memory, electrically erasable programmable read-only memory (EEPROM), programmable read-only memory (PROM), a magnetic memory, a magnetic disk, and an optical disk.

A UI module and an exercise management module may be stored in the memory 130. The UI module and the exercise management module may be software modules or programs including one or more instructions, and may correspond to portions of other programs. The processor 120 may call the UI module and the exercise management module from the memory 130 and execute the instructions corresponding to the UI module and the exercise management module.

The UI module may include a UI input/output module and a UI configuration module. The UI input/output module may identify a user's input for a UI screen displayed on the UI unit 110, and may control an output of an UI element created or changed by the UI configuration module. The UI configuration module may create or change a UI element that is to be displayed on the UI unit 110, according to information identified through the exercise management module, the UI unit 110, or the sensor 140.

The exercise management module may include an exercise process setting module and an exercise state identification module. When a user who wants to use the exercise machine 100 is identified, the exercise process setting module may set an exercise process suitable for the user, based on information about the user. For example, the exercise process setting module may receive exercise process information from the smart gym server 200 through the communication interface unit 150, and may set an exercise process corresponding to the identified user. The exercise state identification module may generate exercise state information of the user, based on a movement of an exercise machine received through the sensor 140, and may generate information representing the progress of the exercise process in which the user's exercise state has been reflected or information representing the exercise result. The exercise state check module may transmit the information representing the progress of the exercise process in which the user's exercise state has been reflected to the UI module or may record the information representing the progress of the exercise process in which the user's exercise state has been reflected in the memory 130.

The sensor 140 may include at least one sensor module for sensing the movement of the exercise machine 100. The sensor 140 may sense the movement of the weight unit of the exercise machine 100 or a manipulation unit that the user's body contacts, and may obtain sensing data corresponding to the sensed movement. The sensing data may be in the form of time, distance, depth, or image. The sensor 140 may include at least one of various types of sensors such as a radar sensor, a time of flight (ToF) type 3D sensor, an ultrasonic sensor, and an infrared image sensor.

The communication interface unit 150 may perform wired/wireless communication with another device or a network. To this end, the communication interface unit 150 may include a communication module that supports at least one of various wired/wireless communication methods. For example, the communication module may include a communication module that performs local communication such as Wireless Fidelity (Wi-Fi), various types of mobile communication such as 3G, 4G, and 5G, or ultra-wideband communication, or a communication module that performs wired communication using coaxial cables or optical cables, but is not limited thereto, and may include various types of communication modules according to the development of communication technology. The communication interface unit 150 may be connected to a device outside the exercise machine 100 and may transmit or receive a message including a signal or data to or from the device. The exercise machine 100 may communicate with the smart gym server 200 or a user terminal (such as a wearable device or a smartphone) or the manager terminal 300 (such as a PC, a laptop, or a smartphone) through the communication interface unit 150.

According to the above-described configuration, the processor 120 of the exercise machine 100 may execute the one or more instructions stored in the memory 130, to control the UI unit 110 to display a first UI element indicating the user's exercise state corresponding to the movement of the exercise machine 100 sensed by the sensor 140 and a second UI element indicating an exercise guide recommended during an exercise using the exercise machine 100 on the UI screen output to the UI unit 110. At this time, the processor 120 of the exercise machine 100 may change the color or shape of at least one of the first UI element and the second UI element, based on a distance between the first UI element and the second UI element on the UI screen. In this regard, a method of changing and displaying UI elements on the UI screen output to the UI unit 110 of the exercise machine 100 to provide an exercise guide to the user using the exercise machine 100 and intuitively know the user's exercise state will now be described in detail with reference to FIGS. 3 through 10.

Figure 3:
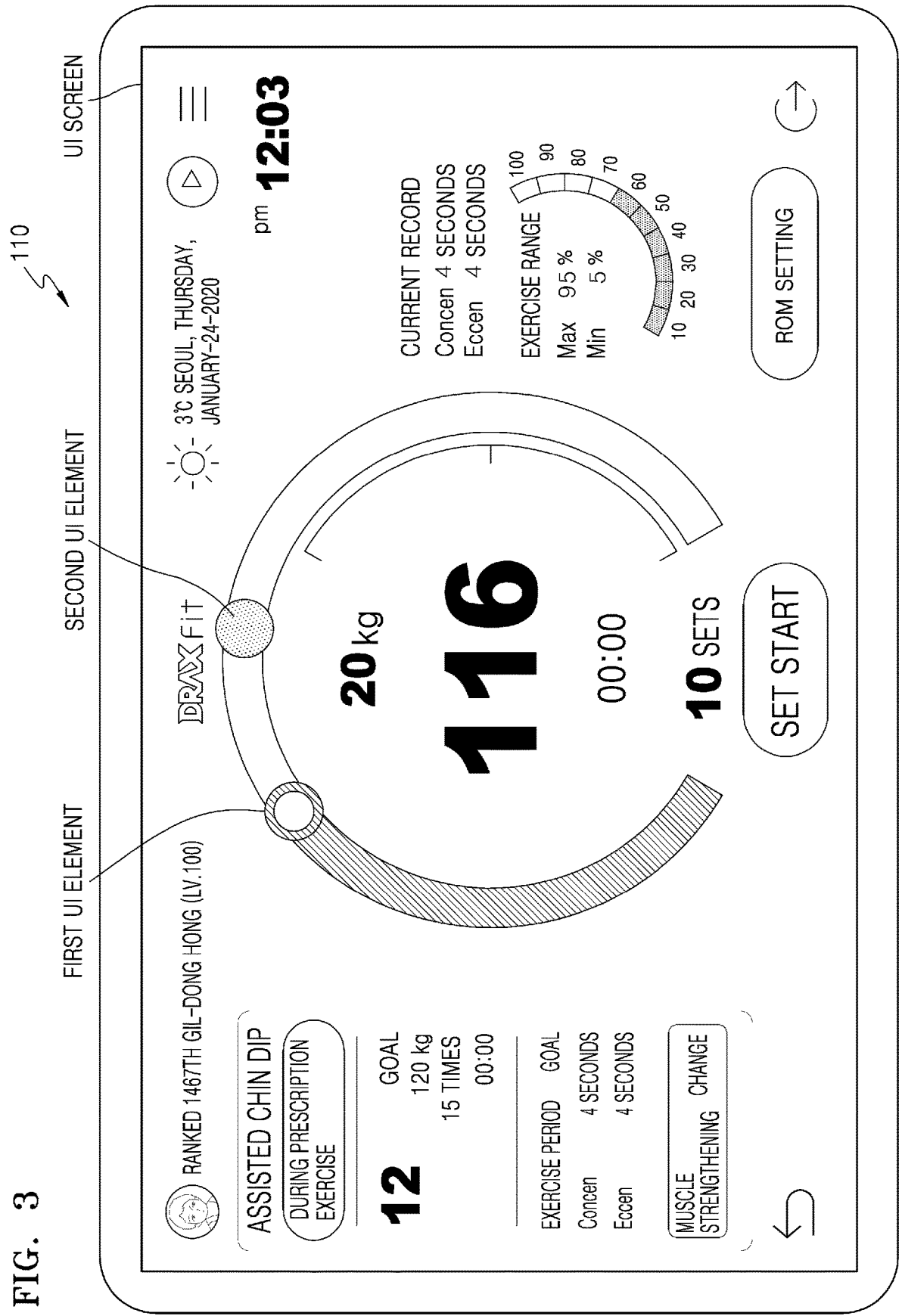
FIG. 3 is a view showing a user interface (UI) screen output to a UI unit 110 of an exercise machine according to an embodiment of the present disclosure.

FIG. 3 is a view showing a UI screen output to the UI unit 110 of the exercise machine 100 according to an embodiment of the present disclosure.

Referring to FIG. 3, the UI unit 110 of the exercise machine 100 may provide an exercise guide to the user, and output a UI screen through which the user's exercise state may be intuitively known. User information, the name of the exercise machine 100, exercise process information, exercise status information, and the like may be displayed on the UI screen.

The exercise process information includes target values such as a weight, the number of sets, and the number of repetitions for each set, and exercise styles according to exercise purposes such as muscle strengthening, a life health, and a diet. When the exercise machine 100 recognizes the user, the exercise process information may be automatically set based on the user's ability level information and exercise performance history information, or may be set according to an exercise program determined in advance by a fitness trainer.

The exercise status information includes weight information during exercise or the user's exercise state. The exercise status information may be displayed on the UI screen in the form of numbers, letters, graphics, and the like. For example, as shown in FIG. 3, the exercise status information may be displayed at the center of the UI screen.

The UI unit 110 of the exercise machine 100 may display a movement line that represents a movable range of the exercise machine 100 and a motion trajectory of the exercise machine 100 on a predetermined area of the UI screen. For example, when the exercise machine 100 is an arm curl machine, a leg curl machine, a leg extension machine, or the like, the moving line may have a curved line shape, and, when the exercise machine 100 is a chest press machine, a shoulder press machine, a lat pull down machine, or the like, the movement line may have a straight line shape. Referring to FIG. 3, it can be seen that information such as a weight during exercise, an exercise time, and the number of exercises is displayed in numbers or letters at the center of the UI screen, and a movement line is displayed in a curved graphic around the information.

A first UI element is a graphic UI representing the user's exercise state corresponding to a movement of the exercise machine 100 detected by the sensor 140, and may also be referred to as a first indicator or a first pointer. A second UI element is a graphic UI representing an exercise guide recommended during an exercise using the exercise machine 100, and may also be referred to as a second indicator or a second pointer.

The processor 120 of the exercise machine 100 may calculate a location of the first UI element within the UI screen, based on the movement of the exercise machine 100 detected by the sensor 140. The processor 120 may control the UI unit 110 to display the first UI element on the UI screen, according to the calculated location. Accordingly, the first UI element may track and display the user's exercise state in real time.

The processor 120 may control the UI unit 110 to display the second UI element on the UI screen, according to pre-defined settings. Because the second UI element serves as an exercise guide recommended during an exercise using the exercise machine 100, the second UI element may be displayed on the UI screen according to a setting corresponding to the user of the exercise machine 100 among a plurality of predefined settings.

The UI unit 120 of the exercise machine 100 may determine locations on which the first UI element and the second UI element are displayed, to reciprocate along the movement line representing the movable range of the exercise machine 100 and the motion trajectory of the exercise machine 100, the movement line being displayed on the predetermined area of the UI screen. For example, the processor 120 may control the UI unit 110 according to predefined settings to make the second UI element appear to reciprocate between a starting point and an ending point of the movement line by the number of repetitions per set. The processor 120 may control the UI unit 110, based on the movement of the exercise machine 100 detected by the sensor 140, to make the first UI element appear to reciprocate in correspondence with a motion speed at which and a motion range in which the user actually exercises.

FIGS. 4A through 8 illustrate an example of changing and displaying the color or shape of at least one of the first UI element and the second UI element according to a distance between the first UI element and the second UI element.

Figure 4A:
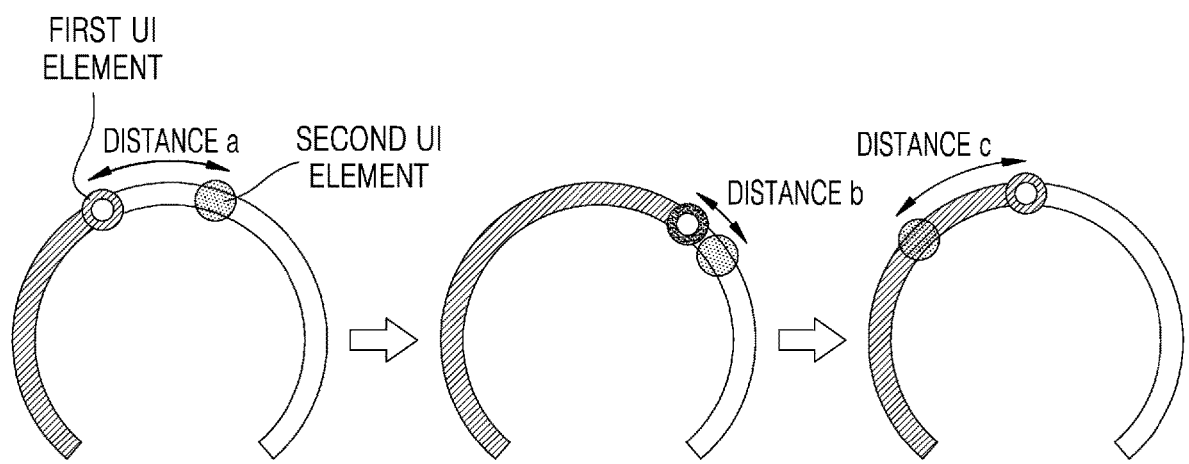
FIGS. 4A, 4B, and 4C illustrate an example of changing and displaying the color of at least one of a first UI element and a second UI element according to a distance between the first UI element and the second UI element.
Figure 4B:
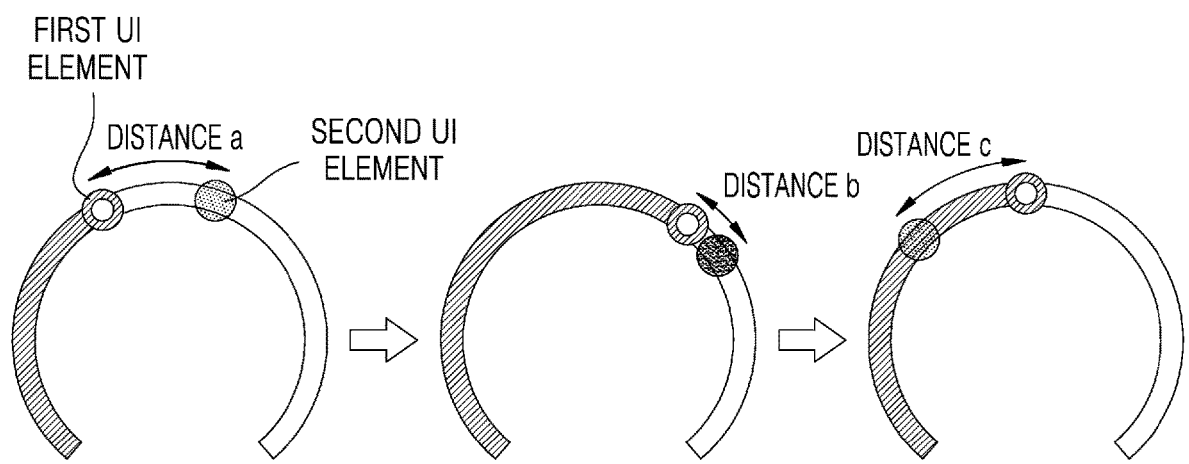
Figure 4C:
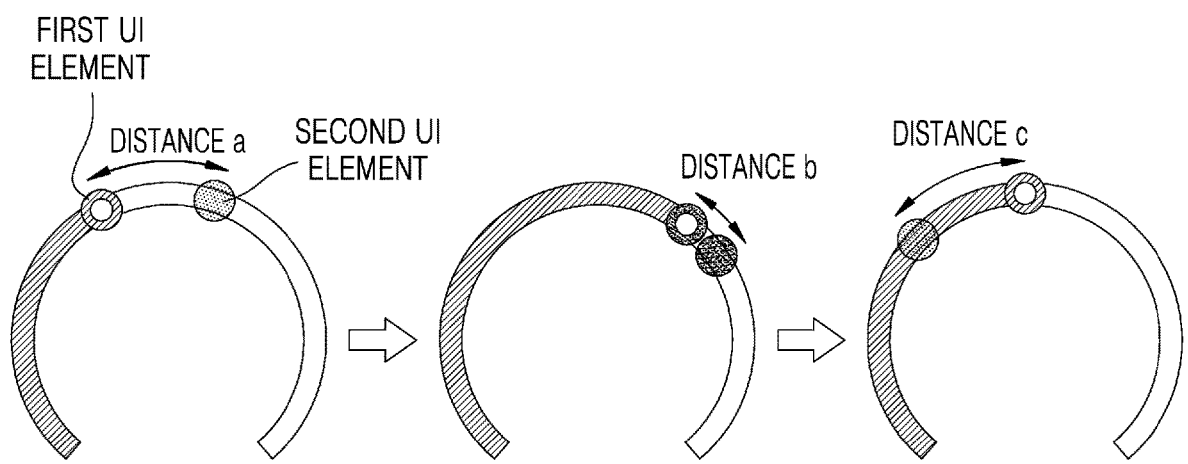

FIGS. 4A, 4B, and 4C illustrate an example of changing and displaying the color of at least one of the first UI element and the second UI element according to the distance between the first UI element and the second UI element.

The processor 120 of the exercise machine 100 may change and display the color of at least one of the first UI element and the second UI element, based on whether the distance between the first UI element and the second UI element becomes smaller or larger than a predetermined threshold.

For example, the processor 120 of the exercise machine 100 may change the color of the first UI element, when the distance between the first UI element and the second UI element falls within a predetermined range. The processor 120 of the exercise machine 100 may change the color of the first UI element, when the distance between the first UI element and the second UI element deviates from the predetermined range.

Referring to FIG. 4A, it can be seen that, when the distance between the first UI element and the second UI element changes from distance 'a' to distance 'b' (distance 'a' is greater than distance 'b'), the color of the first UI element is changed. It can also be seen that, when the distance between the first UI element and the second UI element changes from distance 'b' to distance 'c' (distance 'c' is greater than distance 'b'), the color of the first UI element is again changed.

To sum up the matters shown in FIG. 4A, when the distance between the first UI element and the second UI element narrows from distance 'a' to distance 'b', the color of the first UI element may change, and, when the distance between the first UI element and the second UI element widens from distance 'b' to distance 'c', the color of the first UI element may change again.

As another example, the processor 120 of the exercise machine 100 may change the color of the second UI element, when the distance between the first UI element and the second UI element falls within the predetermined range. The processor 120 of the exercise machine 100 may change the color of the second UI element, when the distance between the first UI element and the second UI element deviates from the predetermined range.

Referring to FIG. 4B, it can be seen that, when the distance between the first UI element and the second UI element is from distance 'a' to distance 'b' (distance 'a' is greater than distance 'b'), the color of the second UI element is changed. It can also be seen that, when the distance between the first UI element and the second UI element is from distance 'b' to distance 'c' (distance 'c' is greater than distance 'b'), the color of the second UI element is again changed.

To sum up the matters shown in FIG. 4B, when the distance between the first UI element and the second UI element narrows from distance 'a' to distance 'b', the color of the second UI element may change, and, when the distance between the first UI element and the second UI element widens from distance 'b' to distance 'c', the color of the second UI element may change again.

As another example, the processor 120 of the exercise machine 100 may change both the colors of the first and second UI elements, when the distance between the first UI element and the second UI element falls within the predetermined range. The processor 120 of the exercise machine 100 may change both the colors of the first and second UI elements, when the distance between the first UI element and the second UI element deviates from the predetermined range.

Referring to FIG. 4C, it can be seen that, when the distance between the first UI element and the second UI element is from distance 'a' to distance 'b' (distance 'a' is greater than distance 'b'), both the colors of the first and second UI elements are changed. It can also be seen that, when the distance between the first UI element and the second UI element is from distance 'b' to distance 'c' (distance 'c' is greater than distance 'b'), both the colors of the first and second UI elements are again changed.

To sum up the matters shown in FIG. 4C, when the distance between the first UI element and the second UI element narrows from distance 'a' to distance 'b', both the colors of the first and second UI elements may change, and, when the distance between the first UI element and the second UI element widens from distance 'b' to distance 'c', both the colors of the first and second UI elements may change again.

Figure 5A:
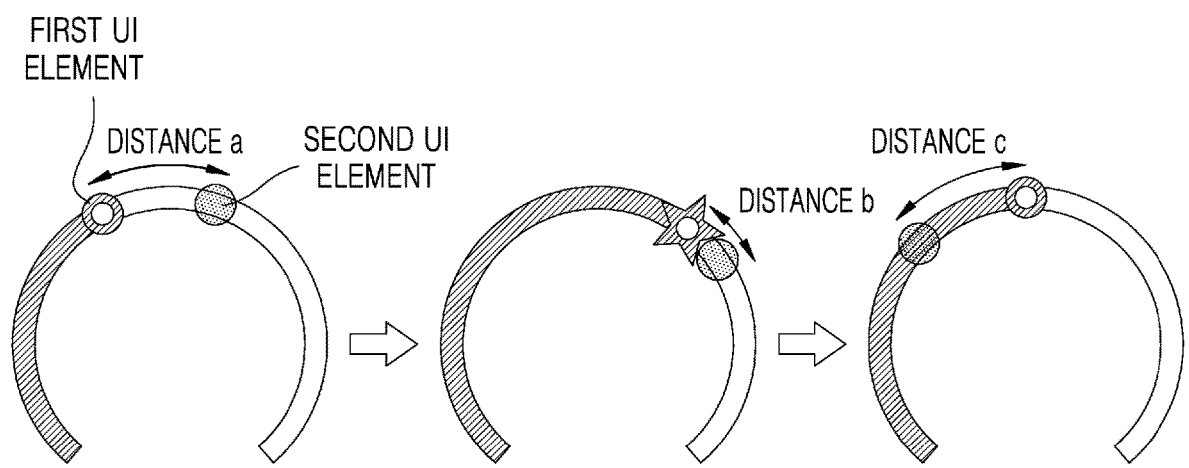
FIGS. 5A, 5B, and 5C illustrate an example of changing and displaying the shape of at least one of the first UI element and the second UI element according to the distance between the first UI element and the second UI element.
Figure 5B:
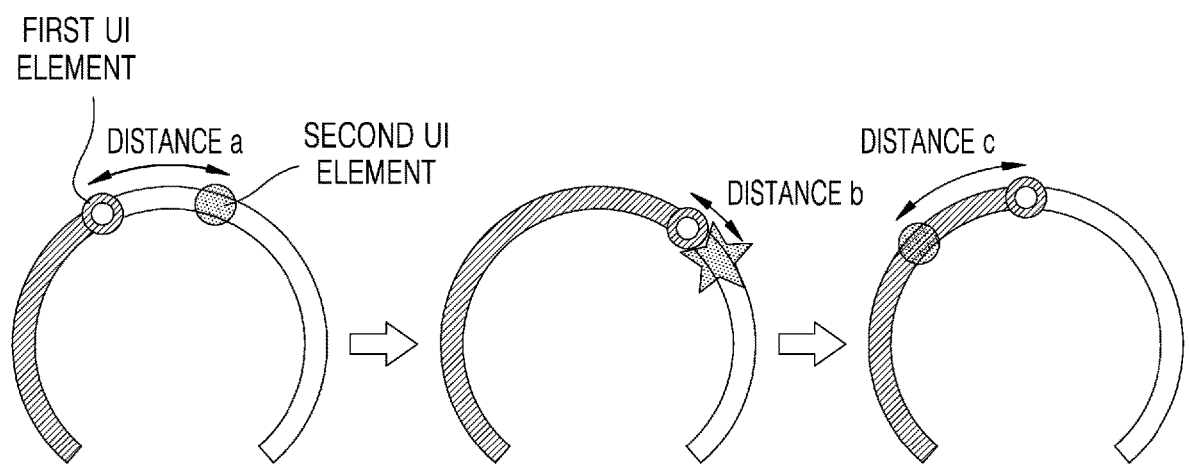
Figure 5C:
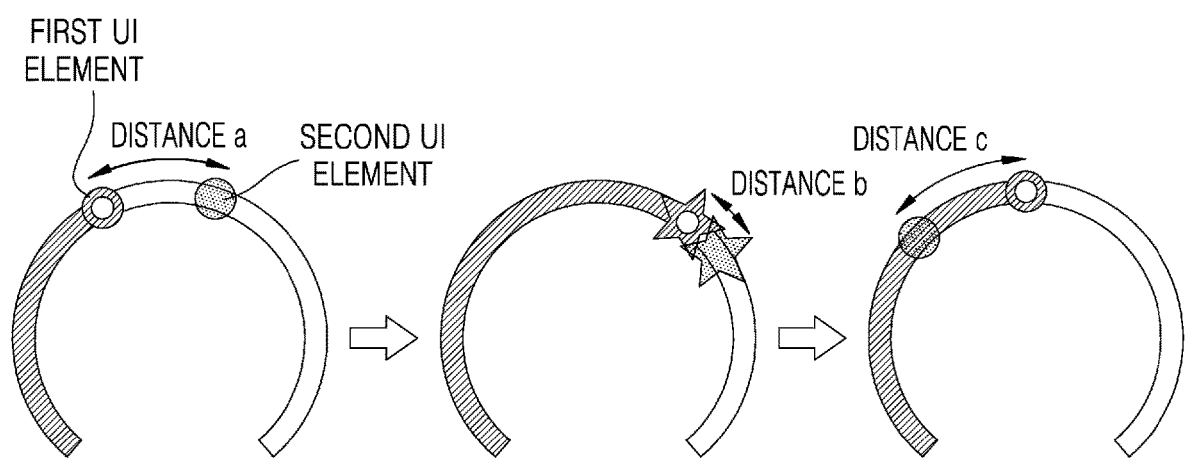

FIGS. 5A, 5B, and 5C illustrate an example of changing and displaying the shape of at least one of the first UI element and the second UI element according to the distance between the first UI element and the second UI element.

The processor 120 of the exercise machine 100 may change and display the shape of at least one of the first UI element and the second UI element, based on whether the distance between the first UI element and the second UI element becomes smaller or larger than a predetermined threshold.

For example, the processor 120 of the exercise machine 100 may change the shape of the first UI element, when the distance between the first UI element and the second UI element falls within a predetermined range. The processor 120 of the exercise machine 100 may change the shape of the first UI element, when the distance between the first UI element and the second UI element deviates from the predetermined range.

Referring to FIG. 5A, it can be seen that, when the distance between the first UI element and the second UI element is from distance 'a' to distance 'b' (distance 'a' is greater than distance 'b'), the shape of the first UI element is changed. It can also be seen that, when the distance between the first UI element and the second UI element is from distance 'b' to distance 'c' (distance 'c' is greater than distance 'b'), the shape of the first UI element is again changed.

To sum up the matters shown in FIG. 5A, when the distance between the first UI element and the second UI element narrows from distance 'a' to distance 'b', the shape of the first UI element may change, and, when the distance between the first UI element and the second UI element widens from distance 'b' to distance 'c', the shape of the first UI element may change again.

As another example, the processor 120 of the exercise machine 100 may change the shape of the second UI element, when the distance between the first UI element and the second UI element falls within the predetermined range. The processor 120 of the exercise machine 100 may change the shape of the second UI element, when the distance between the first UI element and the second UI element deviates from the predetermined range.

Referring to FIG. 5B, it can be seen that, when the distance between the first UI element and the second UI element is from distance 'a' to distance 'b' (distance 'a' is greater than distance 'b'), the shape of the second UI element is changed. It can also be seen that, when the distance between the first UI element and the second UI element is from distance 'b' to distance 'c' (distance 'c' is greater than distance 'b'), the shape of the second UI element is again changed.

To sum up the matters shown in FIG. 5B, when the distance between the first UI element and the second UI element narrows from distance 'a' to distance 'b', the shape of the second UI element may change, and, when the distance between the first UI element and the second UI element widens from distance 'b' to distance 'c', the shape of the second UI element may change again.

As another example, the processor 120 of the exercise machine 100 may change both the shapes of the first and second UI elements, when the distance between the first UI element and the second UI element falls within the predetermined range. The processor 120 of the exercise machine 100 may change both the shapes of the first and second UI elements, when the distance between the first UI element and the second UI element deviates from the predetermined range.

Referring to FIG. 5C, it can be seen that, when the distance between the first UI element and the second UI element is from distance 'a' to distance 'b' (distance 'a' is greater than distance 'b'), both the shapes of the first and second UI elements are changed. It can also be seen that, when the distance between the first UI element and the second UI element is from distance 'b' to distance 'c' (distance 'c' is greater than distance 'b'), both the shapes of the first and second UI elements are again changed.

To sum up the matters shown in FIG. 5C, when the distance between the first UI element and the second UI element narrows from distance 'a' to distance 'b', both the shapes of the first and second UI elements may change, and, when the distance between the first UI element and the second UI element widens from distance 'b' to distance 'c', both the shapes of the first and second UI elements may change again.

Figure 6A:
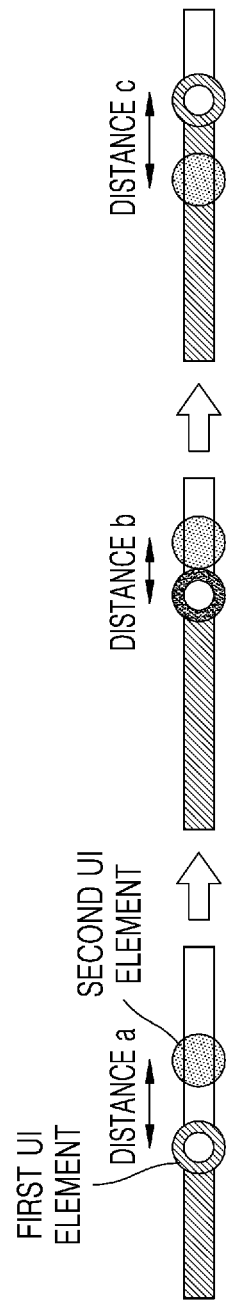
FIGS. 6A, 6B, and 6C illustrate another example of changing and displaying the color of at least one of the first UI element and the second UI element according to the distance between the first UI element and the second UI element.
Figure 6B:
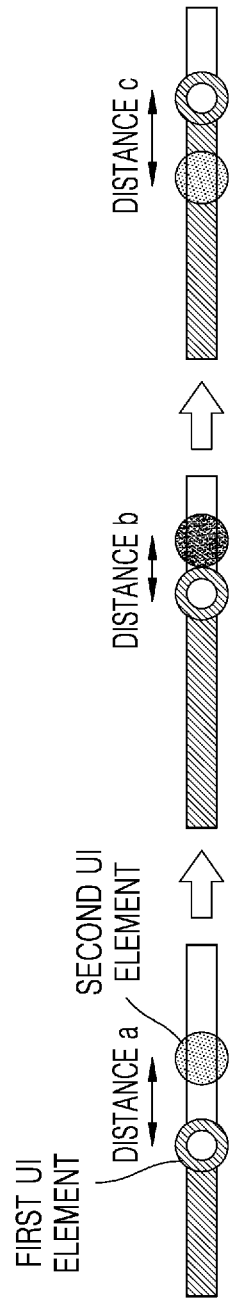
Figure 6C:
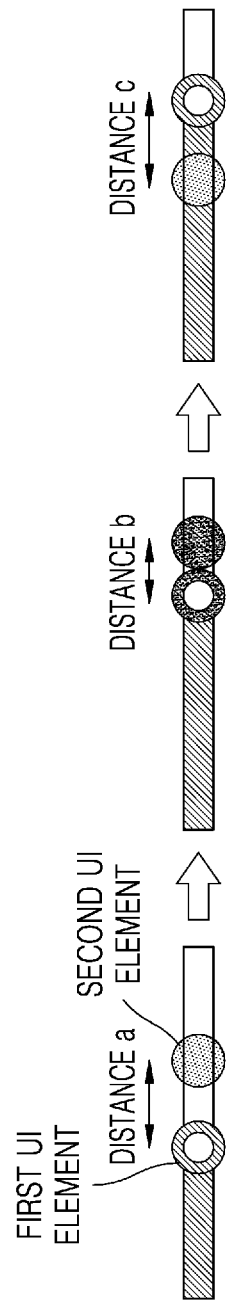

FIGS. 6A, 6B, and 6C illustrate another example of changing and displaying the color of at least one of the first UI element and the second UI element according to the distance between the first UI element and the second UI element.

FIGS. 6A, 6B, and 6C are different from the previously-described FIGS. 4A, 4B, and 4C in that a movement line displayed in a predetermined area of the UI screen is a straight line rather than a curve. When the exercise machine 100 is an arm curl machine, a leg curl machine, a leg extension machine, or the like, because the movement line has a curved line shape, the previously-described UIs of FIGS. 4A, 4B, and 4C may be applied. On the other hand, when the exercise machine 100 is a chest press machine, a shoulder press machine, a lat pull down machine, or the like, because the movement line has a straight line shape, the previously-described UIs of FIGS. 6A, 6B, and 6C may be applied.

Even in the case of a UI having a linear movement line, the shape of at least one of the first UI element and the second UI element may be changed and displayed, as shown in FIGS. 5A, 5B, and 5C.

Figure 7:
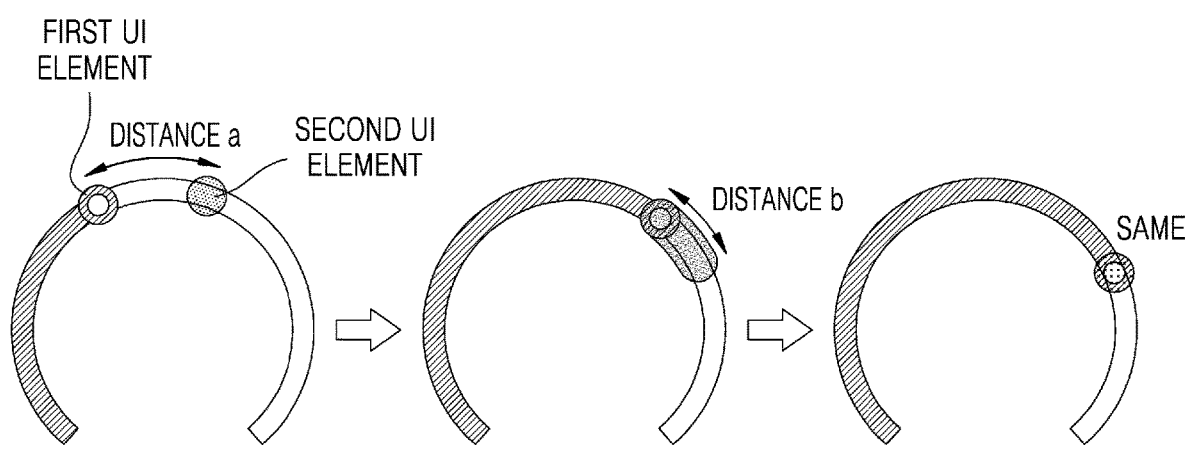
FIG. 7 illustrates an example of changing and displaying the shape of the second UI element, to visually indicate a degree of matching between the first UI element and the second UI element.

FIG. 7 illustrates an example of changing and displaying the shape of the second UI element, to visually indicate a degree of matching between the first UI element and the second UI element.

For example, to visually indicate a degree of matching between the first UI element and the second UI element, the processor 120 of the exercise machine 100 may change the second UI element to have a shape surrounding the first UI element, when the distance between the first UI element and the second UI element falls within the predetermined range. The degree of matching between the first UI element and the second UI element may be a criterion indicating how much the user adheres to the exercise guide while exercising.

Referring to FIG. 7, it can be seen that, when the distance between the first UI element and the second UI element is distance 'a', the first and second UI elements are each displayed on the movement line. When the first UI element approaches the second UI element and falls within the predetermined range, for example, when the distance between the first UI element and the second UI element becomes from distance 'a' to distance 'b', as shown in FIG. 7, the processor 120 of the exercise machine 100 may change the second UI element to have a shape surrounding the first UI element. As the degree of matching between the first UI element and the second UI element increases, the processor 120 may change an area by which the second UI element surrounds the first UI element to decrease. As the degree of matching between the first UI element and the second UI element decreases, the processor 120 may change the area by which the second UI element surrounds the first UI element to increase. When the distance between the first UI element and the second UI element deviates from the predetermined range, the first and second UI elements may be changed again to be each displayed on the movement line.

Figure 8:
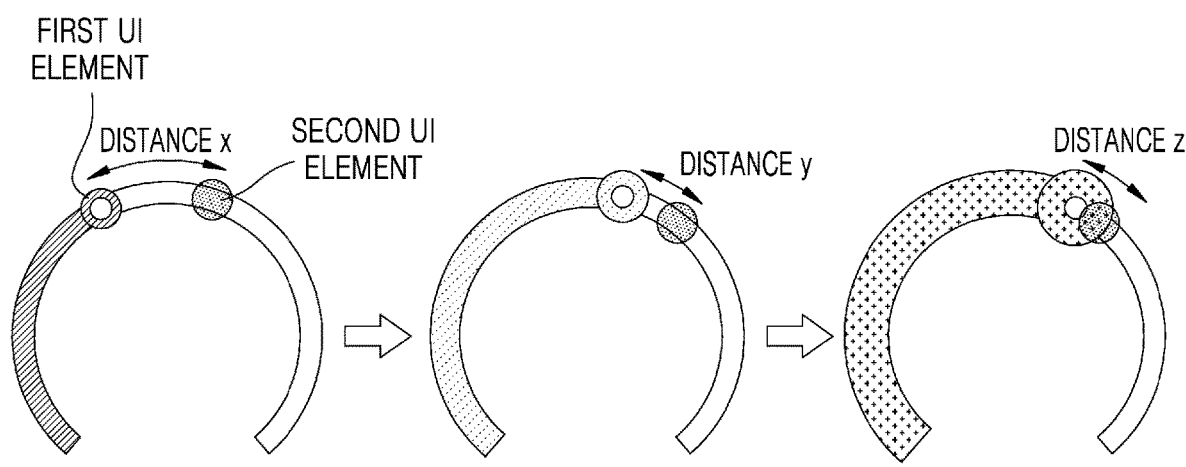
FIG. 8 illustrates an example of changing and displaying the size of the first UI element, according to the distance between the first UI element and the second UI element.

FIG. 8 illustrates an example of changing and displaying the size of the first UI element, according to the distance between the first UI element and the second UI element.

For example, the processor 120 of the exercise machine 100 may change the size of the first UI element to increase, as the distance between the first UI element and the second UI element decreases. Referring to FIG. 8, a change in the first UI element can be seen when the distance between the first UI element and the second UI element is distance 'x', distance 'y', and distance 'z' (distance 'x'>distance 'y'>distance 'z'). As shown in FIG. 8, as the distance between the first UI element and the second UI element decreases, the size of the first UI element is increased to motivate the user to exercise according to the exercise guide.

The processor 120 of the exercise machine 100 may change the color or thickness of a UI element indicating the amount of change from the start point of the movement line displayed on the predetermined area of the UI screen to a current location of the first UI element, based on the distance between the first UI element and the second UI element. As shown in FIG. 8, as the distance between the first UI element and the second UI element decreases, the processor 120 of the exercise machine 100 may change the color of the UI element indicating the amount of change up to the current location of the first UI element or may increase the thickness of the UI element.

For example, the processor 120 of the exercise machine 100 may make the distance between the first UI element and the second UI element correspond to one of a plurality of distance sections, and may change the color or shape of at least one of the first UI element and the second UI element for each of the plurality of distance sections. In this case, the plurality of distance sections may have different lengths from each other. The respective lengths of the plurality of distance sections may be pre-set by the user or determined by a predetermined function. For example, when the distance between the first UI element and the second UI element belongs to one of a total of three distance sections, the processor 120 of the exercise machine 100 may change the color or shape of at least one of the first UI element and the second UI element to a color or shape corresponding to the distance section.

Figure 9:
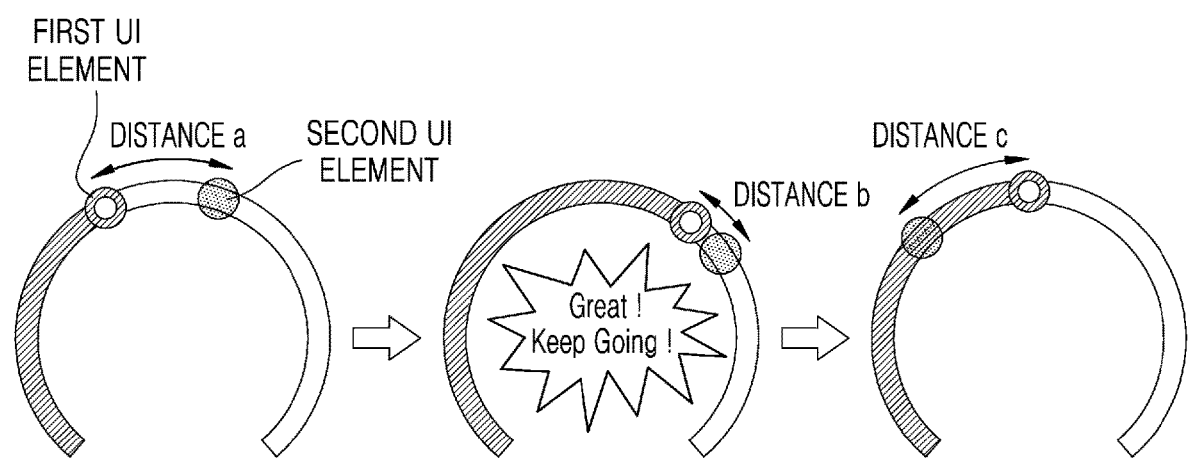
FIG. 9 is a view for explaining an operation of a UI unit when the distance between the first UI element and the second UI element falls within a specific range corresponding to a predetermined degree of matching.

FIG. 9 is a view for explaining an operation of a UI unit when the distance between the first UI element and the second UI element falls within a specific range corresponding to a predetermined degree of matching.

For example, the processor 120 of the exercise machine 100 may control the UI unit 110 to output a sound or display including a specific message, when the distance between the first UI element and the second UI element corresponds to the specific range corresponding to the predetermined degree of matching.

Referring to FIG. 9, it can be seen that, when the distance between the first UI element and the second UI element is distance 'a', the first and second UI elements are each displayed on the movement line. When the first UI element approaches the second UI element and falls within the specific range corresponding to the predetermined degree of matching, for example, when the distance between the first UI element and the second UI element becomes from distance 'a' to distance 'b', the UI unit 110 may output a sound 'Great! Keep Going' or a display 'Great! Keep Going'. When the distance between the first UI element and the second UI element deviates from the predetermined range, the processor 120 of the exercise machine 100 may stop outputting a sound or display including a specific message.

Figure 10:
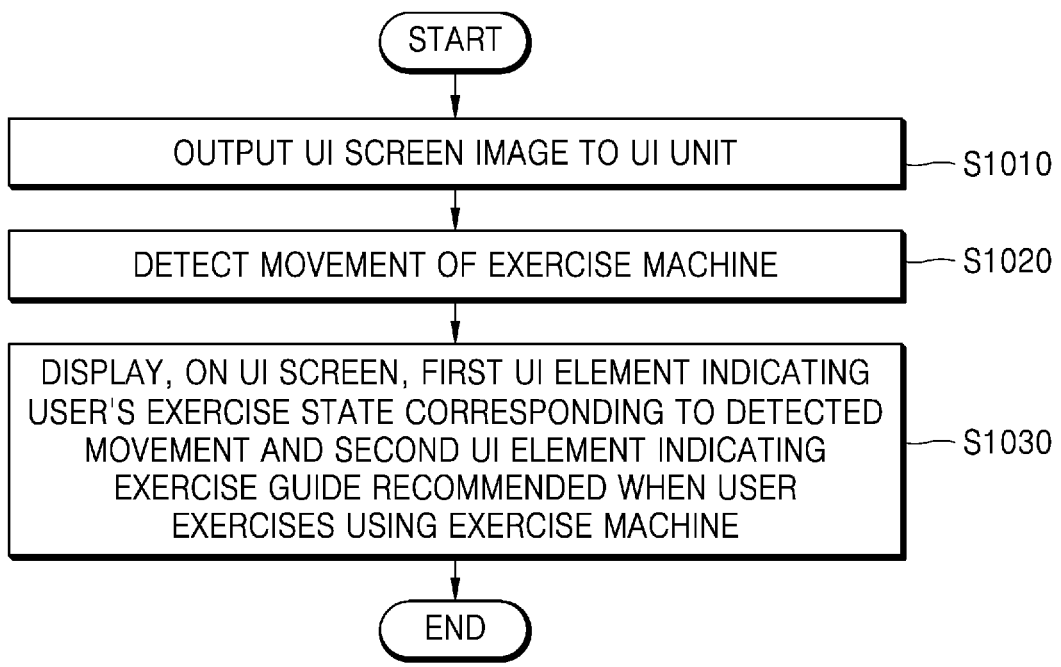
FIG. 10 is a flowchart of a method of controlling a UI of an exercise machine, according to an embodiment of the present disclosure.

FIG. 10 is a flowchart of a method of controlling a UI of the exercise machine 100. Although omitted, descriptions of the exercise machine 100 given above are also applicable to the UI controlling method.

In operation S1010, the exercise machine 100 may output a UI screen image to the UI unit 110. When the user is recognized or starts exercising, or when there is a manipulation of the UI unit 110 by the user, the exercise machine 100 may output a UI screen to the UI unit 110.

In operation S1020, the exercise machine 100 may detect a movement of the exercise machine 100 through the sensor 140. The exercise machine 100 may sense, through the sensor 140, a movement of the weight unit of the exercise machine 100 or the manipulation unit that the user's body contacts.

In operation S1030, the exercise machine 100 may display, on the UI screen, the first UI element indicating the user's exercise state corresponding to the movement detected by the sensor 140 and the second UI element indicating the exercise guide recommended during an exercise using the exercise machine 100. The exercise machine 100 may change and display the color or shape of at least one of the first UI element and the second UI element, based on the distance between the first UI element and the second UI element on the UI screen.

For example, when the distance between the first UI element and the second UI element falls within the predetermined range, the exercise machine 100 may change and display the color or shape of at least one of the first UI element and the second UI element. On the other hand, when the distance between the first UI element and the second UI element deviates from the predetermined range, the exercise machine 100 may change and display the color or shape of at least one of the first UI element and the second UI element.

For example, the exercise machine 100 may change the size of the first UI element to increase, as the distance between the first UI element and the second UI element decreases.

For example, to visually indicate a degree of matching between the first UI element and the second UI element, the exercise machine 100 may change the second UI element to have a shape surrounding the first UI element, when the distance between the first UI element and the second UI element falls within the predetermined range. As the degree of matching between the first UI element and the second UI element increases, the exercise machine 100 may change an area by which the second UI element surrounds the first UI element to decrease. As the degree of matching between the first UI element and the second UI element decreases, the processor 120 of the exercise machine 100 may change the area by which the second UI element surrounds the first UI element to increase. When the distance between the first UI element and the second UI element deviates from the predetermined range, the first and second UI elements may be changed to be each displayed on the movement line.

The exercise machine 100 may make the distance between the first UI element and the second UI element correspond to one of a plurality of distance sections, and may change the color or shape of at least one of the first UI element and the second UI element for each of the plurality of distance sections. In this case, the plurality of distance sections may have different lengths from each other.

The exercise machine 100 may output a sound or display including a specific message, when the distance between the first UI element and the second UI element corresponds to the specific range corresponding to the predetermined degree of matching.

Any one of the above-described embodiments of the present disclosure may be combined with the other examples unless they are incompatible with each other.

The above-described method of controlling a UI of the exercise machine 100 may be embodied in form of a computer-readable recording medium storing processor-executable instructions. A computer is a device capable of calling stored instructions from a recording medium and operating according to the disclosed embodiments according to the called instructions, and may include the exercise machines 100 according to the disclosed embodiments. Examples of the computer-readable recording medium may include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, a magnetic tape, a floppy disk, a magneto-optical data storage device, an optical data storage device, a hard disk, a solid-state disk (SSD), and any device capable of storing an instruction or software, related data, a data file, and data structures and providing the instruction or software, the related data, the data file, and the data structures to a processor or a computer such that the processor or the computer execute the instruction.

Methods according to the disclosed embodiments may be provided in the form of a computer program. Such a computer program may include an application in the form of a software program electronically distributed through a manufacturer of the weight exercise machine 100 or a server of a third party, or an online content market such as an application store. In addition, such a computer program may be stored in a storage medium of a server, the weight exercise machine 100, or a storage medium of the weight exercise machine 100, and the server or the weight exercise machine 100 may execute the computer program to implement the methods according to the disclosed embodiments.

The invention claimed is:

1. An exercise machine comprising:
 a sensor configured to detect a movement of the exercise machine;
 a user interface (UI) unit configured to output a UI screen;
 a memory storing one or more instructions; and
 a processor configured to execute the one or more instructions to control the UI unit to display, on the UI screen, a first UI element indicating, in real time, a user's exercise state corresponding to the detected movement and a second UI element indicating an exercise guide recommended during an exercise using the exercise machine,
 wherein the processor is further configured to:
 control the UI screen such that the second UI element showing the exercise guide appears to reciprocate between a start point and an end point of a movement line by a number of repetitions per set, the movement line being configured to visualize a movement range and a motion trajectory of the exercise machine;
 change and display a color or a shape of at least one of the first UI element and the second UI element, based on a real-time distance between the first UI element and the second UI element on the UI screen, wherein the processor is further configured to execute the one or more instructions to make the distance between the first UI element and the second UI element correspond to one of a plurality of distance sections, and change the color or the shape of the at least one of the first UI element and the second UI element for each of the plurality of distance sections.

2. The exercise machine of claim 1, wherein the processor is further configured to execute the one or more instructions to, when the distance between the first UI element and the second UI element falls within a predetermined range, change the color or the shape of the at least one of the first UI element and the second UI element.

3. The exercise machine of claim 2, wherein the processor is further configured to execute the one or more instructions to change the second UI element to have a shape surrounding the first UI element, when the distance between the first UI element and the second UI element falls within the predetermined range, to visually indicate a degree of matching between the first UI element and the second UI element.

4. The exercise machine of claim 3, wherein the processor is further configured to execute the one or more instructions to, as the degree of matching between the first UI element and the second UI element increases, decrease an area by which the second UI element surrounds the first UI element, and, as the degree of matching between the first UI element and the second UI element decreases, increase the area by which the second UI element surrounds the first UI element.

5. The exercise machine of claim 2, wherein the processor is further configured to execute the one or more instructions to, as the distance between the first UI element and the second UI element decreases, increase a size of the first UI element.

6. The exercise machine of claim 1, wherein the processor is further configured to execute the one or more instructions to, when the distance between the first UI element and the second UI element deviates from a predetermined range, change the color or the shape of the at least one of the first UI element and the second UI element.

7. The exercise machine of claim 1, wherein the plurality of distance sections have different lengths from each other.

8. The exercise machine of claim 1, wherein the processor is further configured to execute the one or more instructions to control the UI unit to, when the distance between the first UI element and the second UI element corresponds to a specific range corresponding to a predetermined degree of matching, output a sound or display including a specific message.

9. The exercise machine of claim 1, wherein the processor is further configured to execute the one or more instructions to change a color or a thickness of a UI element indicating the amount of change from the start point of the movement line displayed on a predetermined area of the UI screen to a current location of the first UI element, based on the distance between the first UI element and the second UI element, the movement line representing a movable range of the exercise machine and a motion trajectory of the exercise machine.

10. A method of controlling an exercise machine, the method comprising:
   outputting a user interface (UI) screen to a UI unit;
   detecting a movement of the exercise machine; and
   controlling, performed by a processor, the UI screen, a first UI element indicating, in real time, a user's exercise state corresponding to the detected movement and a second UI element indicating an exercise guide recommended during an exercise using the exercise machine,
   wherein the controlling of the UI screen comprises:
   controlling the UI screen such that the second UI element showing the exercise guide appears to reciprocate between a start point and an end point of a movement line by a number of repetitions per set, the movement line being configured to visualize a movement range and a motion trajectory of the exercise machine; and
   changing and displaying a color or a shape of at least one of the first UI element and the second UI element, based on a real-time distance between the first UI element and the second UI element on the UI screen,
   wherein the displaying comprises making the distance between the first UI element and the second UI element correspond to one of a plurality of distance sections, changing the color or the shape of the at least one of the first UI element and the second UI element for each of the plurality of distance sections, and displaying at least one of the first UI element and the second UI element having the changed color or shape.

11. The method of claim 10, wherein the displaying comprises, when the distance between the first UI element and the second UI element falls within a predetermined range, changing the color or the shape of at least one of the first UI element and the second UI element.

12. The method of claim 11, wherein the displaying comprises changing and displaying the second UI element to have a shape surrounding the first UI element to visually indicate a degree of matching between the first UI element and the second UI element, when the distance between the first UI element and the second UI element falls within the predetermined range.

13. The method of claim 12, wherein the displaying comprises, as the degree of matching between the first UI element and the second UI element increases, decreasing an area by which the second UI element surrounds the first UI element and displaying the decreased area, and, as the degree of matching between the first UI element and the second UI element decreases, increasing the area by which the second UI element surrounds the first UI element and displaying the increased area.

14. The method of claim 11, wherein the displaying comprises, as the distance between the first UI element and the second UI element decreases, increasing a size of the first UI element and displaying the first UI element having the increased size.

15. The method of claim 10, wherein the displaying comprises, when the distance between the first UI element and the second UI element deviates from a predetermined range, changing the color or the shape of the at least one of the first UI element and the second UI element.

16. The method of claim 10, wherein the plurality of distance sections have different lengths from each other.

17. The method of claim 10, further comprising, when the distance between the first UI element and the second UI element corresponds to a specific range corresponding to a predetermined degree of matching, outputting a sound or display including a specific message.

18. A computer-readable storage medium storing instructions executable by a processor, the computer-readable storage medium comprising:
   instructions to output a user interface (UI) screen to a UI unit;
   instructions to detect a movement of an exercise machine; and
   instructions to display, on the UI screen, a first UI element indicating, in real time, a user's exercise state corresponding to the detected movement and a second UI element indicating an exercise guide recommended during an exercise using the exercise machine,
   wherein the instructions to display, on the UI screen, comprise:
   controlling the UI screen such that the second UI element showing the exercise guide appears to reciprocate between a start point and an end point of a movement line by a number of repetitions per set, the movement line being configured to visualize a movement range and a motion trajectory of the exercise machine; and
   changing and displaying a color or a shape of at least one of the first UI element and the second UI element, based on a real-time distance between the first UI element and the second UI element on the UI screen,
   wherein the displaying comprises making the distance between the first UI element and the second UI element correspond to one of a plurality of distance sections, changing the color or the shape of the at least one of the first UI element and the second UI element for each of the plurality of distance sections, and displaying at least one of the first UI element and the second UI element having the changed color or shape.

* * * * *